United States Patent
Tanghoej

(10) Patent No.: US 7,670,331 B2
(45) Date of Patent: Mar. 2, 2010

(54) DEVICE FOR OPENING A HUMAN BLADDER

(75) Inventor: Allan Tanghoej, Kokkedal (DK)

(73) Assignee: Coloplast A/S, Humlebaek (DK)

( * ) Notice: Subject to any disclaimer, the term of this patent is extended or adjusted under 35 U.S.C. 154(b) by 726 days.

(21) Appl. No.: 10/539,777

(22) PCT Filed: Dec. 19, 2003

(86) PCT No.: PCT/DK03/00922

§ 371 (c)(1),
(2), (4) Date: Jun. 20, 2005

(87) PCT Pub. No.: WO2004/056290

PCT Pub. Date: Jul. 8, 2004

(65) Prior Publication Data

US 2006/0116661 A1 Jun. 1, 2006

(30) Foreign Application Priority Data

Dec. 20, 2002 (DK) .............................. 2002 01972

(51) Int. Cl.
- A61M 1/00 (2006.01)
- A61M 27/00 (2006.01)
- A61M 31/00 (2006.01)
- A61M 5/32 (2006.01)
- A61M 25/00 (2006.01)

(52) U.S. Cl. .............. 604/544; 604/163; 604/540; 604/278; 604/528

(58) Field of Classification Search .......... 604/544, 604/528, 164.03, 540, 163, 278
See application file for complete search history.

(56) References Cited

U.S. PATENT DOCUMENTS

| 3,630,206 | A | | 12/1971 | Gingold | |
|---|---|---|---|---|---|
| 4,170,996 | A | * | 10/1979 | Wu | 604/171 |
| 4,237,894 | A | * | 12/1980 | Cohen | 604/104 |
| 4,487,808 | A | * | 12/1984 | Lambert | 428/423.1 |
| 4,571,241 | A | * | 2/1986 | Christopher | 604/104 |
| 4,664,113 | A | * | 5/1987 | Frisbie et al. | 606/194 |
| 4,692,149 | A | * | 9/1987 | Rosenberg et al. | 604/99.02 |
| 4,737,147 | A | | 4/1988 | Ferrando et al. | |

(Continued)

FOREIGN PATENT DOCUMENTS

EP 0 873 760 A1 10/1998

(Continued)

OTHER PUBLICATIONS

Zinner, N.R., et al., "Measuring Softness of Inner Female Uretha", Dept. Of Surgery (Urology), Oct. 1983, vol. XXII, No. 4, pp. 444-445.

(Continued)

Primary Examiner—Tatyana Zalukaeva
Assistant Examiner—Susan Su
(74) Attorney, Agent, or Firm—Daniel G. Chapik

(57) ABSTRACT

A device for urinary catheterization including an oblong member for opening the human bladder and a guide member for manipulating the oblong member. The guide member may be provided in a bent configuration, e.g. being curled or folded, such that the size of the device is small in comparison with the size of known catheters, especially in comparison with existing catheters for male users.

15 Claims, 3 Drawing Sheets

U.S. PATENT DOCUMENTS

| | | | |
|---|---|---|---|
| 4,771,773 A * | 9/1988 | Kropf | 606/108 |
| 4,909,785 A * | 3/1990 | Burton et al. | 604/544 |
| 5,117,838 A * | 6/1992 | Palmer et al. | 600/585 |
| 5,242,398 A * | 9/1993 | Knoll et al. | 604/103.05 |
| 5,456,667 A * | 10/1995 | Ham et al. | 604/107 |
| 5,562,622 A | 10/1996 | Tihon | |
| 5,865,815 A | 2/1999 | Tihon | |
| 5,871,475 A | 2/1999 | Frassica | |
| 5,887,593 A | 3/1999 | Levius | |
| 5,916,195 A * | 6/1999 | Eshel et al. | 604/96.01 |
| 5,969,223 A * | 10/1999 | Nagai et al. | 73/1.06 |
| 6,033,413 A * | 3/2000 | Mikus et al. | 606/108 |
| 6,231,564 B1 * | 5/2001 | Gambale | 604/528 |
| 6,248,100 B1 * | 6/2001 | de Toledo et al. | 604/540 |
| 6,290,666 B1 * | 9/2001 | Devonec | 623/1.16 |
| 6,379,334 B1 * | 4/2002 | Frassica | 604/165.04 |
| 6,416,545 B1 | 7/2002 | Mikus et al. | |
| 6,482,348 B1 * | 11/2002 | Wang et al. | 264/514 |
| 6,849,070 B1 * | 2/2005 | Hansen et al. | 604/544 |
| 7,220,491 B2 * | 5/2007 | Rouns et al. | 428/520 |
| 2002/0103467 A1 * | 8/2002 | Kubalak | 604/327 |
| 2002/0123739 A1 * | 9/2002 | Haacke et al. | 604/544 |
| 2003/0153899 A1 * | 8/2003 | Eshel et al. | 604/544 |
| 2003/0167069 A1 * | 9/2003 | Gonzales et al. | 606/200 |
| 2005/0070882 A1 * | 3/2005 | McBride | 604/544 |
| 2006/0025753 A1 * | 2/2006 | Kubalak et al. | 604/544 |
| 2006/0111691 A1 * | 5/2006 | Bolmsjo et al. | 604/544 |
| 2007/0088330 A1 * | 4/2007 | House | 604/544 |

FOREIGN PATENT DOCUMENTS

| | | |
|---|---|---|
| SE | 415 447 | 10/1980 |
| WO | WO 02/36192 A1 | 5/2002 |
| WO | WO 03/002179 A2 | 1/2003 |

OTHER PUBLICATIONS

Zinner, N.R., et al., "Evaluation of Inner Urethral Softness", Dept. Of Surgery (Urology), Oct. 1983, vol. XXII, No. 4, pp. 446-448.

* cited by examiner

Fig. 3a
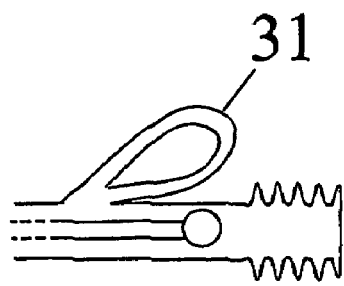
Fig. 3b
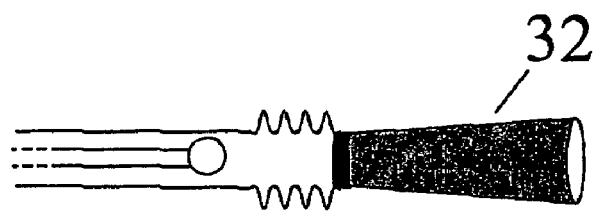
Fig. 3c
Fig. 3
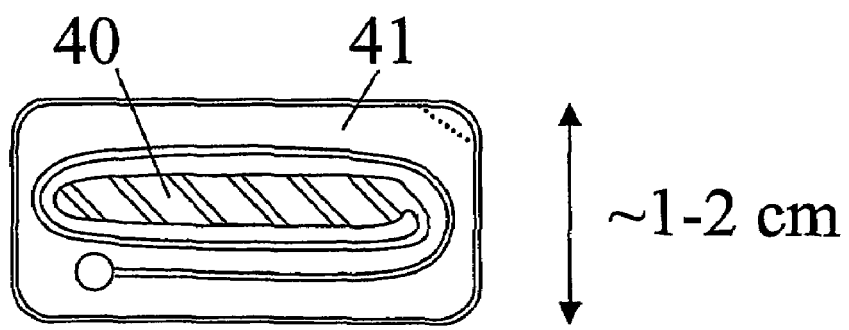
~1-2 cm
Fig. 4

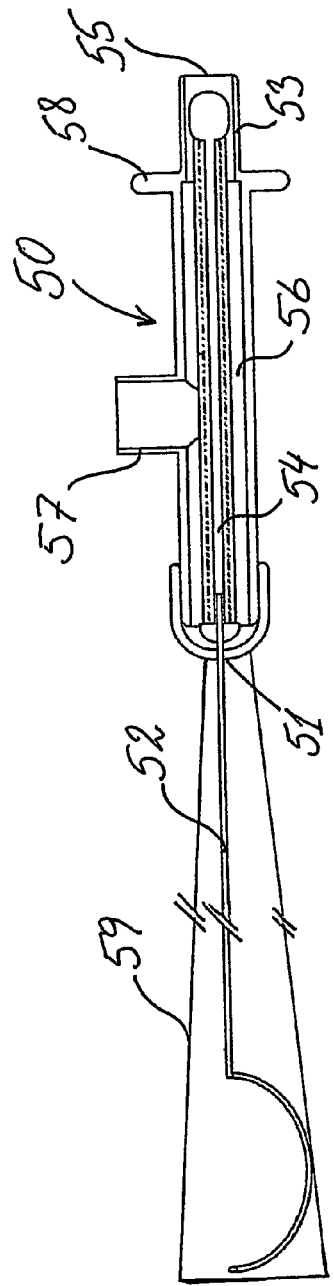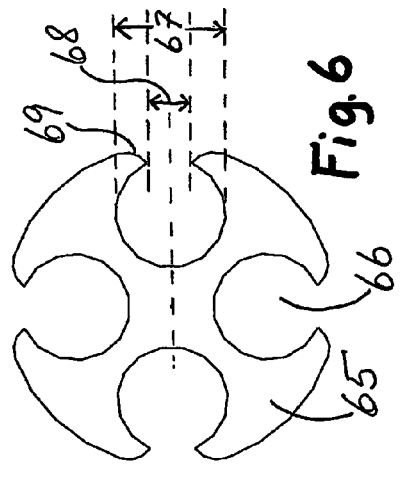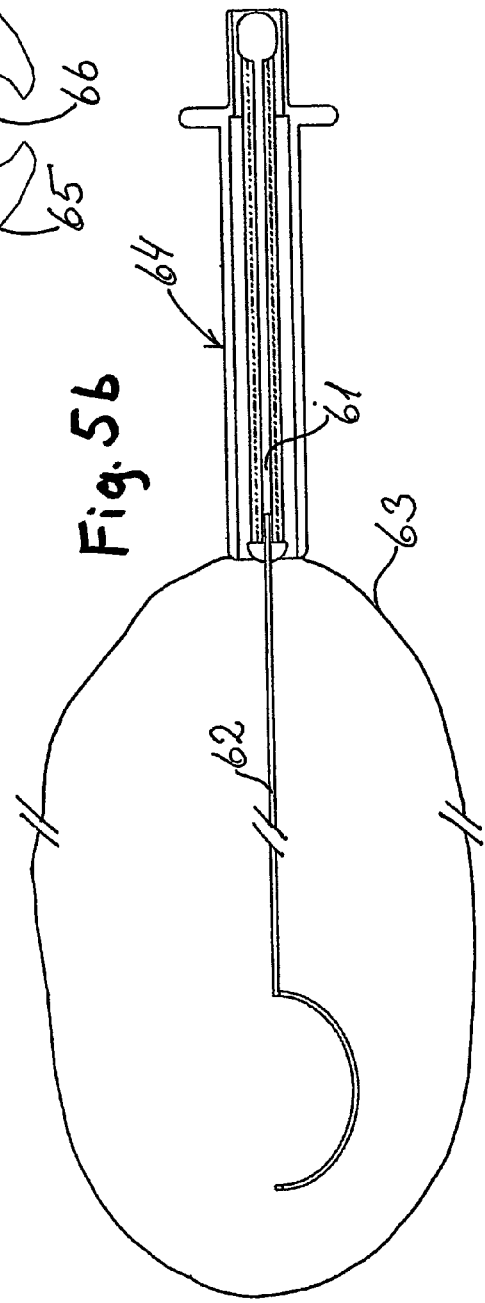

DEVICE FOR OPENING A HUMAN BLADDER

FIELD OF THE INVENTION

The present invention relates to a device for opening a bladder for draining fluids from the bladder. In particular, the invention relates to a device that can be arranged in a configuration wherein the size of the device is small in comparison with the size of known catheters, especially in comparison with existing catheters for male users.

BACKGROUND OF THE INVENTION

Persons suffering from urinary incontinence or disabled individuals who may not be able to control urination, normally use catheters to void their bladder. Existing catheters are typically made from a single piece of a continuous catheter tube, and typically, the thickness of the catheter tube is constant throughout its length. The length of the catheter is chosen to allow the catheter to be inserted into the urethra until the urine starts to flow. In addition, a certain over-length of the catheter is available for the manipulation and removal of the catheter. The over-length, inter alia, supports the user to firmly hold the catheter, to guide the urine to a place of disposal and to withdraw the catheter safely, without risking that the catheter disappears into the urethra. The catheter is thus longer than the urinary canal and, especially for men, the total length of the known catheters prevents carrying and disposal of the catheter in a discrete manner.

It is important that the tubular member does not collapse or kink, since this may cause problems during insertion and withdrawal of the catheter from a urinary canal and further may cause blocking of the passage for the urine to drain through the catheter. Existing catheters are therefore typically made from, e.g., PVC or polyurethane to form a form stabile and relatively hard, but still bendable, tube. Since the hardness of the catheter tube is selected to be relatively high with the view to avoid kinking or collapse of the internal flow channel, the catheters may collapse if they are bent with a too small radius of curvature. Accordingly, existing catheters not only have considerable lengths but they are also typically packed in an elongate condition, and in order to maintain the functioning of the catheter, the user is prevented from bending such packages into smaller or less notable dimensions.

Therefore, the existing catheters may be troublesome to handle and to bring along, not least for the large group of catheter users, who make use of catheters on a daily basis.

DESCRIPTION OF THE INVENTION

It is an object of a preferred embodiment of the present invention to overcome the aforesaid disadvantages of the known catheters by providing a device for opening a human bladder comprising an oblong member for opening the urethral sphincter. The oblong member comprising means for draining fluid from the bladder, and a guide member for manipulating the oblong member, wherein the guide member in a first configuration is bent and the guide member allows unfolding from said first configuration into a second configuration allowing for insertion of the oblong member in a urinary tract.

Accordingly, a device allowing draining of the bladder is provided. In a preferred embodiment of the invention the oblong member is shorter than the guide member in said second configuration, i.e. in the second configuration the guide member constitutes a major part of the length of the device, such as at least 50% of the length of the device. Since the oblong member is manipulated via a guide member, the oblong member can be provided in a length which is just sufficient to open the urinary sphincter and which is very short compared with the length of a regular catheter. In this regard, the sphincter refers to at least one of the inner and the outer sphincter. In one embodiment, it may be an advantage to provide the oblong member in a length sufficient to provide a free passage through the prostate or even in a length which is sufficient to provide a free passage around the prostate and simultaneously to open the sphincter. The residual length necessary for manipulating the oblong member into a position for opening the urethral sphincter and for draining urine from the bladder is provided by the guide member in the second configuration. At least a part of the guide member is thus adapted to be inserted in the urethra.

The cross-sectional area, i.e. the area inside the periphery of a cross-section perpendicular to the length direction of the catheter, of a major part of the guide member at least in said first configuration is preferably substantially smaller than the cross-sectional area of the oblong member. The guide member may thus in said second configuration be essentially tubular with a cross sectional area similar to that of the oblong member, whereas in said first configuration the cross sectional area of the guide member is reduced by transverse collapsing of the guide member resulting in a more elongated cross-section of reduced cross-sectional area.

In one embodiment of the invention, the cross sectional area of a major part of the guide member, in said second configuration, is smaller than the cross-sectional area of the oblong member. In this case the guide member may, e.g., be a rod-like element, which is relatively thin compared to the oblong member or the cavity of the urinary tract The guide member may, e.g., be bent by folding and/or rolling the guide member. In one embodiment of the invention, the guide member in said first configuration is rolled, e.g., into a circular or elliptical configuration. The catheter may be bent such that one or more sections are rotated at least 180 degrees relative to a straight configuration or even 360 degrees to make at least one loop or winding.

The guide member may be bent into said first configuration and unfolded into said second configuration. The transition from the first configuration to the second configuration may be reversible.

As the oblong member may be relatively short and the guide member is flexible in that the guide member supports unfolding from a first configuration in which the guide member is bent, into the second configuration and the guide member in said first configuration has a cross sectional area smaller than the cross sectional area of the oblong member, it is possible to arrange the device in a configuration wherein the device is discrete and easy to convey and dispose, e.g., in a configuration in which the guide member is rolled up or folded, e.g., into a first configuration, in which the guide member is substantially circular or substantially elliptical. Thereby the longitudinal extension of the guide member may be reduced to make the shape of the device more compact in the first configuration than in the second configuration. In one embodiment of the invention, the guide member is rolled or folded to have at least one circular or elliptical winding with a diameter essentially equal to the length of the oblong member.

According to one embodiment, the device may be provided with a guiding member allowing bending by rolling and/or folding into a first configuration, e.g., a substantially circular or substantially elliptical configuration, without or at least substantially without causing plastic or permanent deformation of the guide member. Also, it may be an advantage to provide the oblong member in a material and/or a shape supporting bending or rolling up or folding of the oblong member for storage in a shorter and more discrete configuration.

A device according to the invention may in particular be advantageous when the device is adapted for opening a human bladder in a male, i.e., the length of the device with the guide member in its second configuration is comparable to the length of the male urethra. Due to length of the male urethra as compared to the female urethra, regular catheters for males are longer than for females, and it is thus particularly desirable to provide such a device in a compact configuration in which the device is discrete and easy to convey and dispose. However a device according to the invention may also advantageously be adapted for opening a human bladder in a female.

In one embodiment of the invention at least a part of the guide member in said first configuration is bent by an essentially elastic deformation of the guide member. The bending may, e.g., be a folding and/or rolling the guide member. By an essentially elastic deformation, a guide member previously deformed by application of a force, such as by being constrained by a packing element, such as a package for housing the catheter, will tend to revert to its former shape when the force is removed. The guide member need not possess perfect elasticity to be essentially elastic, as long as a substantial part of the deformation is elastic. Also materials deforming perfectly elastically, i.e., reverting completely to their former shape, are rare and typically long-term storage, such as more than a few days, adds to reduced shape memory. Elasticity of the guide member may also be brought about mechanically by the mechanical structure of the guide member or braiding.

According to another embodiment, the guide member may deform plastically. In this case a force must be applied to unfold the guide member. The guide member may be bent by an essentially plastic deformation, i.e., the change of shape due to an applied force is permanent in the sense that the element tends to keep the imposed shape even when the force is removed.

In one embodiment of the invention at least a part of the guide member is rolled up in a rolled first configuration, i.e., a configuration wherein the guide member is smoothly curved without kinking, e.g., a circular or elliptical configuration.

In one embodiment of the invention at least a part of the guide member in said first configuration is folded into a folded configuration, i.e., bending of the guide member is essentially restricted to discrete zones of the guide member, said zones constituting a minor part of the total length of the guide member wherein the guide member may kink or sections of the guide member may be disconnected, while sections of the guide member in between said discrete zones are essentially unchanged from the first configuration to the second configuration.

At least a part of the guide member could be provided in two or more longitudinal sections, which in the second configuration are joined end to end, and in the first configuration are arranged to reduce the length of the guide member, e.g., by arranging the sections side by side. In this case the sections could be relatively rigid elements. Such a guide member provided in sections may in particular be useful in an embodiment, wherein the cross-sectional area of the guide member in the first and even in the second configuration, is smaller than the cross-sectional area of the oblong member. The sections may be connected, e.g., by rotational joints or joined with a string, which could be elastic, reaching through the hollow sections. In this case elasticity of the guide member may be brought about by the mechanical construction, e.g., if the shapes of the sections are such that a straight configuration results when the string is tightened. In one embodiment of the invention the number of sections comprised in the guide member is so large that the guide member may be essentially rolled.

In a preferred embodiment of the invention the guide member allows storage in the first configuration, i.e., the guide member should endure storage in the first configuration without losing desired properties, such as the capability of being unfolded into an operable second configuration. The guide member should at least allow short-term storage, i.e., storage for a few hours or even a day. This allows the user to bring along the device in a discrete configuration. Preferably the guide member should allow storage in the first configuration even for a period on the order of months or a few years.

In a preferred embodiment of the invention, the guide member allow elastic deformation and is retained in the first configuration by retaining means. The retaining means could, e.g., be included in or constitute a part of a package. In one embodiment of the invention, the device is packed in a first configuration and the guide member is adapted to unfold into the second configuration upon un-packaging of the device. It is advantageous that the guide member be able to at least partly unfold by itself into the second configuration or at least into a configuration, which is easily transformed to a configuration suitable for insertion of the oblong member, as this reduces the need for touching parts of the device to be inserted in the body. Thereby the risk of contamination is reduced. The guide member should allow storage in the first configuration without losing its ability to unfold when released, e.g., from a package.

Preferably, the device is packed for storage and delivery to the user in a rolled and/or folded configuration, and, preferably, the device is adapted to unroll upon opening of the package, i.e., the guide member could preferably be made to automatically take or at least support easy configuration into a shape wherein it can be used for guiding the oblong member through the urinary canal to the sphincter, e.g., a substantially straight configuration. This could be obtained with a guide member supporting essentially elastic deformation.

In a preferred embodiment of the invention, the guide member may be fixed to the oblong member. The guide member and the oblong member may be made as one integral part, i.e., made in one piece. For example, the guide member and the oblong member may be cast together, or the guide member may be extruded from the oblong member. Alternatively, the guide member may be attachable to the oblong member. The guide member and the oblong member may be made separately, and afterwards, be firmly attached together. A firm and reliable joint can be achieved, e.g., by gluing or welding the two members together. A reliable and secure joint between the oblong member and the guide member may be imperative in order to ensure that the oblong member can easily be removed from the urethra after the bladder has been voided. However, as will be discussed below, it may also be advantageous to provide the device with a guide member which is attachable to the oblong member, or a device where the guide member is detachable, even during use. For some embodiments of the inventions, there is no need for the guide member to be attached to the oblong member. Thus the guide member may be adapted to engage the oblong member in a loose connection. These aspects will be further elaborated upon below.

The guide member serves firstly to manipulate the oblong member, i.e., to insert the oblong member in the urethral sphincter so that the sphincter can be opened and the bladder voided. The purpose of the oblong member is to provide a passage for urine through the sphincter. Since the oblong member is inserted into the urethral sphincter via the urinary canal, the oblong member should preferably have an outer cross-sectional size similar to the cross-sectional size of known catheters. The length of the oblong member should preferably be at least slightly longer than the sphincter. Thereby, it is possible to hold the full length of the sphincter open while a part of the tip of the oblong member protrudes into the inside of the bladder. Alternatively, it is possible to hold the sphincter and the passage past the prostate open while a part of the tip protrudes into the inside of the bladder. The length of the oblong member may therefore be less than half the length of a regular male catheter, such as less than a third of the length of a regular male catheter, such as between 1 and 12 cm, such as between 1 and 9 cm, such as between 1 and 7 cm, such as between 3 and 5 cm.

In one embodiment of the invention, at least one conduit is formed exteriorly as a groove in an outer surface of the catheter element, so as during use to form a conduit between a urinary canal of a catheter user and the catheter element. The passage for urine through the sphincter may thus be provided by at least one exterior conduit formed between a urinary canal of a catheter user and the catheter. The oblong member may thus be solid, as the conduit may be provided by one or more grooves starting at the tip or in the vicinity of the tip of the oblong member. In this respect, it may be an advantage to make a smoothly rounded tip. The grooves should continue along the oblong member to a point sufficiently far away from the starting point to ensure that urine could pass the sphincter and/or prostate through the groove. The groove or grooves may follow a helix-like path along the outer surface of the oblong member or it may run in one or more straight or parallel lines along the outer surface of the oblong member. In the case of more than one helix-like curved grooves, the grooves may run intertwined along the member. The groove (s) should be deep enough to allow fluids to flow steadily along the conduit(s) formed between the wall of the urinary canal of a catheter user and the catheter. In order to allow the urine to drain freely, grooves with a depth between 0.2 and 1.5 mm, such as between 0.3 and 1.2 mm, may be provided. The cross-sectional area of the groove or of the sum of the cross-sectional areas of all of the grooves should preferably be comparable to the cross-sectional area of the drainage conduit of catheters known per se. The edges of the grooves may be smooth in order to minimize the risk for irritation of the inside of the urinary canal due to a shape change in the oblong member. The grooves may extend to the outermost part of tip of the oblong member so that urine may flow as soon as the oblong member starts to protrude into the bladder. In a cross-sectional view of the oblong member, the groove or grooves may have a semi-circular shape, a heart shape, an oval shape, a V-shape or in fact any shape which allows urine to drain between the wall of the urinary canal and the catheter.

In another embodiment of the invention, the oblong member comprises a canal through the oblong member with at least one inlet opening and at least one outlet opening allowing drainage of the bladder through the canal. Thus a conduit through the sphincter may be provided via a canal with at least one inlet opening and at least one outlet opening which allows fluid to pass though the member, and thereby allows drainage of the bladder through the canal. With respect to the dimensions of the oblong member, regular catheter dimensions may be employed, i.e., the outer cross-sectional size and the cross-sectional size of the conduit may be chosen in accordance with existing standard sizes for regular catheters. The length of the oblong member may be in the range of 1-7 cm such as in the range of 3-5 cm.

The oblong member may be essentially form-stabile in order to provide an opening of the sphincter, but also to substantially maintain its shape during insertion and retraction of the member. The oblong member is to be inserted into a urinary canal and therefore this part may be made in a flexible and resilient material so that, during insertion, it follows the course of the canal without posing substantial pain or malaise. The oblong member could be made from a thermoplastic elastomer or other thermoplastic materials or from a curable elastomer material or any mixture or combination thereof. Thermoplastic elastomer materials may comprise materials like Polyurethane elastomers (e.g. Estane™), Polyether-blockamide elastomers (e.g. Pebax™) Polyester elastomers (e.g. Hytrel™), poly-olefin elastomers (e.g. Santoprene™ and e.g. Engage™), Polystyrene elastomers (e.g. Kraton™ compounds) and PP elastomers with controlled tactic and atactic domains. Other thermoplastic materials may comprise PVC, e.g. plasticised PVC, Polyethylene homo- or co-polymers, polypropylene homo- or co-polymers, Polyamide types, Polyester types, fluorine-containing thermoplastic materials such as fluorine-containing elastomers among others. Curable elastomer materials may comprise silicone elastomers and curable polyurethane elastomers among others.

The guide member should on one hand be able to support rolling up but on the other hand be rigid enough to support at least insertion of the oblong member, and in some cases also removal of the oblong member after the catheterization has ended. In the second configuration the guide member should thus endure longitudinal compression without collapsing or buckling during insertion in the urethra.

The guide member may be made from a metal or metal alloy with a flexibility permitting rolling up of the guide member. Alternatively, it may be made from a polymer material, either as a solid material, or as a hollow element. As an example, the hollow element may be composed of two oblong concave profiles assembled along their longest edges to form a hollow, tubular member. The guide member may also be made from a composite material, such as kevlarm or similar fibres, such as carbon fibres, polyester fibres or glass fibres. The fibres may be embedded in a resin of the aforementioned kind, e.g., in a polyester resin.

In order to facilitate the manipulation of the device, the guide member may comprise gripping means such as a ring into which a finger may be inserted, a knob, or an area in the distal end of the guide member which is provided with a rough surface so that a firm grip may be facilitated due to increased friction in said end. In another embodiment, the guide member may, at a non-insertable end zone, have a larger size, thus facilitating easier handling. The guide member may also curve to form a handgrip.

In the aforementioned embodiments, the urine should, after it has passed the sphincter, continue its flow in direct contact with the urinary canal of the catheter user. Even though this may have a flushing effect which may have a positive bacteriological effect on the urinary canal, it may sometimes be an advantage to provide a slack tube for guiding the urine inside the urethra or similar urinary canal of the user. The slack tube enables that the urine can be drained to a place of disposal, e.g., to a collection bag. Thus, by providing a slack tube for guiding the urine, a better control of the urine is obtained, especially if, e.g., the urine should be collected in a collection bag. Since the slack tube may extend outside the body, the slack tube may also be used for the extraction of the oblong member from the urinary canal. Accordingly, one preferred embodiment of the invention relates to a device further comprising a slack tube providing an internal conduit for draining urine from the bladder. The slack tube should be arranged in relation to the oblong member so that the internal conduit is in fluid communication with a conduit of the oblong member. The urine, after it has passed the sphincter via the oblong member, is at one proximal end of the slack tube collected inside the conduit thereof and drained out of the urinary canal inside the slack tube. At the other distal end of the slack tube, the urine may be drained into a place of disposal such as a lavatory or a urinary collection bag. Preferably, the slack tube is provided with a structure which is different from the structure of the oblong member. In particular, the slack tube is much more flexible than the oblong member thus allowing the slack tube to be rolled or folded or in any similar way to be arranged in a configuration wherein it takes up less space. The slack tube may be extruded from the oblong member and thereby constitute an integral part of the oblong member. Alternatively, a slack tube may be made separately from the oblong member for subsequent assembling therewith, e.g., by gluing or welding of the slack tube to the oblong member. The slack tube may be made from the same or a similar material as the oblong member. The slack tube may, e.g., be made from a polymer material. However, preferably, the slack tube is made to be less rigid than the oblong member. The slack tube may have a structure which is similar to the structure of a balloon or a condom, i.e., the thickness of the slack tube wall may be a fraction of a millimeter. Such a structure provides virtually no resistance towards bending or folding. The length of the slack tube could be such that the tube extends beyond the external opening of the urinary canal when the corresponding oblong member is in a position wherein it opens the sphincter. At this distal end of the slack tube, connecting means for connecting the tube, e.g., to a collection bag for collection of urine, may be provided. In order to allow easy connection of the slack tube to a collection bag, the slack tube may be longer than the guide member. The device may be delivered to the customer in a configuration wherein the slack tube is rolled up like a condom. During use, the oblong member is inserted into the urethra and, by means of the guide member, it is pushed to a position wherein the sphincter is opened and urine starts to drain. During the insertion operation, the slack tube is unrolled and before the sphincter is passed and urine starts to flow through the slack tube, the distal end thereof may be connected to a place of disposal, e.g., a urinary collection bag.

In order to further ease manipulation of the device, especially the removal of the oblong member, the slack tube may comprise gripping means allowing the user to grip the slack tube for removing the oblong member from a urinary canal. The gripping means may comprise a ring adhered or welded to the slack tube, or the gripping means may be a section with a surface structure so that a high friction is obtained to aid a better grip. The high frictional section should preferably be limited to a part of the device which is not inserted into the urinary canal. For a device comprising a slack tube, a guide member may be necessary in order to insert the oblong member, whereas the slack tube itself may be used for the removal of the oblong member from the urinary canal. Furthermore, the guide member may hinder the extraction of the oblong member and it may hinder the passage of the urine through the urinary canal. Therefore, it may be advantageous that the guide member can be detached from the oblong member once the oblong member is in place in the urethral sphincter. The guide member may be separated from the oblong member even during insertion of the oblong member in the urinary canal, as the guide member may push the oblong member into the urinary canal, even if the guide member is not attached to the oblong member.

The slack tube may also comprise connection means for connecting the slack tube to other elements, e.g., to a collecting reservoir. In one simple embodiment, the connection means could be a conical member similar to connectors for a urinary catheter. In an alternative embodiment, the connection means could comprise a more sophisticated snap locking arrangement, e.g. of the kind known from the LuerLock™ system for medical hoses.

In order to ease the insertion, at least the part including the oblong member may have a surface with low frictional characteristics. On this part, the surface could correspond to the surface of a regular gel-lubricated catheter, a hydrophilic catheter or any catheter known per se. If the device comprises a slack tube, also the surface of the slack tube may be low frictional. However, in order to improve manipulation of the device, the guide member and/or the slack tube or at least the non-insertable parts thereof may be provided with a non-slippery characteristic.

DETAILED DESCRIPTION OF THE INVENTION

Preferred embodiments of the invention will now be described in details with reference to the drawings.

FIG. 3 illustrates the invention comprising a slack tube and includes a side view in FIG. 3a, and two different features that can be added to the slack tube in FIG. 3b and FIG. 3c.

FIG. 4 illustrates the invention wrapped in a package.

FIG. 5 illustrates alternative embodiments of a device including a guiding device and includes a guiding device sealed within a compartment in FIG. 5a, and a guiding device with a receptacle in FIG. 5b.

FIG. 6. illustrates an alternative cross-sectional shape of the oblong member.

Figure 1:
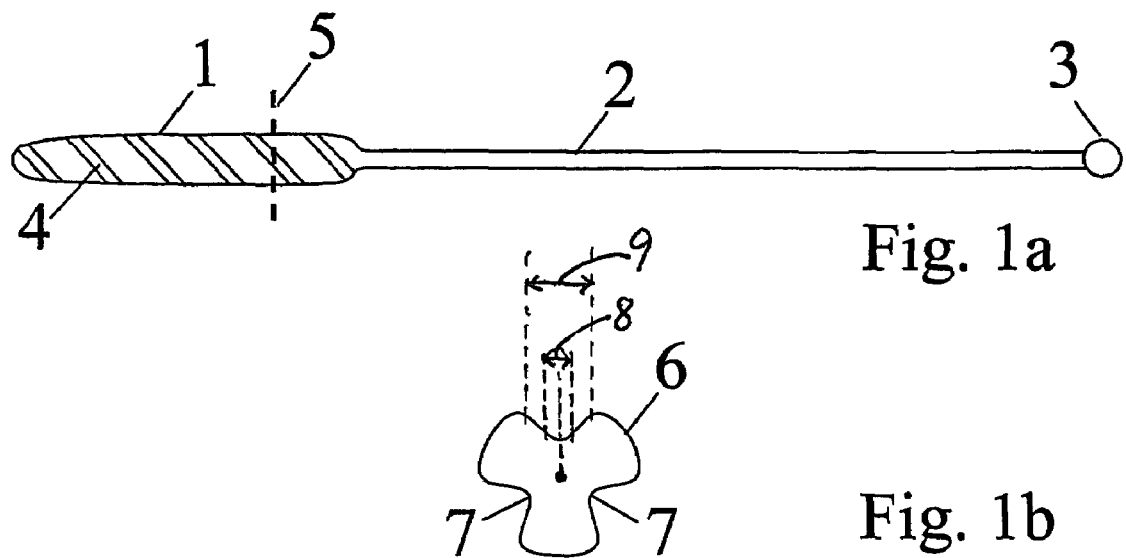
FIG. 1 illustrates a first embodiment of the invention and includes a side view in FIG. 1a and a cross-sectional view in FIG. 1b.

In FIG. 1a a preferred embodiment of a device for opening a human bladder is shown. The device comprises an oblong member 1 made from a flexible polymer material. The oblong member is inserted into the urethra in order to open the sphincter for voiding the bladder. The oblong member is attached to a guide member 2, made out of a flexible polymer. To facilitate the manipulation of the device, i.e., the insertion and retraction of the device, the guide member is provided with a gripping means 3. The oblong member comprises grooves 4, through which grooves urine is drained from the bladder, since conduits are formed between the outer surface of the grooves and the inner surface of the urine canal. Urine thus starts to flow along the grooves when the tip of the oblong member is inside the bladder. The length of the oblong member is such that it is longer than the urethral sphincter; after passage of the sphincter, the urine flows along the urine canal. In FIG. 1b is shown a cross-section 6 of the oblong member obtained along the line 5 in FIG. 1a. In this example, three grooves 7 are intertwined and running along the oblong member, however, any number of intertwined grooves can be used. In this embodiment, the width of the grooves 7, when seen in a cross-sectional view, widens out from a smaller width 8 towards a larger width 9 in the vicinity of the outer periphery of the oblong member.

Figure 2:
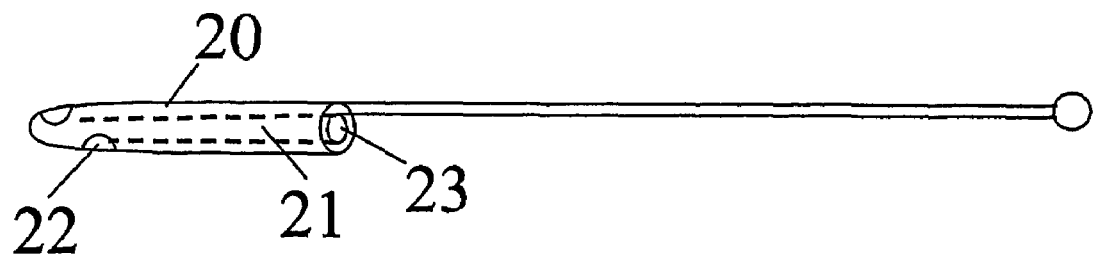
FIG. 2 illustrates a second embodiment of the invention.

In FIG. 2 another preferred embodiment of the device is sketched. The difference with respect to the embodiment shown in FIG. 1a is that the conduit 21 provided by the oblong member 20 includes an inner canal connected to two inlets 22 in the tip of the oblong member. Thus in this embodiment the oblong member is hollow. Upon insertion of the oblong member in the urethral sphincter, the bladder will start to be voided when the inlets reach the inside of the bladder, and urine will pass through the sphincter along the conduit 21 and flow into the urine canal via the outlet 23 in the oblong member. Two inlets are shown, but one, three or more inlets may also be used. The edge around the opening of the outlet 23 should preferably be smoothly rounded in order not to damage the mucosal lining during use.

In FIG. 3a, the device of FIG. 1a is further equipped with a slack tube 30. The slack tube has been extruded from the oblong member and therefore it is an integral part of the oblong member. The slack tube is thus also made from the same material as the oblong member, i.e., a polymer material. The thickness of the slack tube wall is only a fraction of a millimeter. The texture of the slack tube is to be compared with that of a strong plastic bag, and it provides virtually no resistance towards bending or folding. In FIGS. 3b and 3c, two features which can be added to the slack tube are shown. These features may also both be added to a single slack tube. In FIG. 3b, a gripping means 31 has been added. A plastic ring has been adhered either by gluing, or by welding it to the slack tube. By gripping the ring it may be easier to extract the device from the urethra. In FIG. 3c, a connection means 32 has been added. The connection means can be used for connecting the slack tube to a reservoir for collecting the urine.

In FIG. 4, the device 40 of FIG. 3a is shown in a package 41 prior to use. The guide member is made in such a way that the elasticity of the guide member allows the member to be rolled into a rolled configuration, which is maintained while the device is wrapped in a package, but upon opening of the package the guide member is adapted to unroll, or to be unrolled. Thus the present invention provides a device for catheterization which is very handy to store or to bring along especially in comparison with existing catheters for male users, which may be more than 30 mm long, and which do not support bending.

FIG. 5a illustrates a guiding device 50 for guiding the guide member 52 and for guiding the urine to an outlet for controlled drainage of the bladder. The sealing penetration 51 provides a liquid tight seal between the guiding device and the guide member 52. During use, the sealing member 53 is brought into a sealing connection with the opening of the urinary canal of the user. The flange 58 ensures against unintended insertion of the guiding device 50 into the urinary canal. Subsequently, the oblong member 54 is pushed into the urinary canal by the guide member 52 until urine starts to drain. The urine drains through the urinary canal into the inlet opening 55 and further through the conduit 56 of the guiding device 50 to the outlet 57. From the outlet, the urine may be drained into a place of disposal, e.g., into a urinary collection bag. For that purpose, the outlet may be provided with a flange for connection to a collection bag. The inlet as well as the outlet may, until use, be closed by a sealing cap. The inlet as well as the outlet may be provided with means for connecting the cap, a bag or an ampoule of water or similar lubricating substance. Furthermore, the openings could be sealed, e.g., by a foil. In this way, the device may be delivered under sterile conditions to the user, e.g., together with an amount of a lubricating substance, water or a gel, comprised in the conduit 56 of the guiding device. In this regards, the guide member 52, may be sterile sealed within a compartment 59, e.g., within a bag formed from a thin foil. The sealing penetration 51 and/or the outlet 57 may be located anywhere on the guiding device, e.g., as shown in FIG. 5a or 5b.

In FIG. 5b, an embodiment of the guiding device 64 including a receptacle in the form of a urinary collection bag is shown. In this embodiment, the oblong member 61 and the guide member 62 may be enclosed in the receptacle formed by the urinary collection bag 63 and the guiding device 64. During use, the urine is drained directly into the collection bag and, accordingly, the transition between the collection bag and the guiding device 64 is not necessarily sealed. In case the oblong member is to be stored in a friction reducing substance, a seal between the guiding device and the collection bag may preferably be provided. Such a seal may be broken in connection with insertion of the oblong member into the urinary canal, e.g., automatically upon removal of the oblong member from the guiding device.

FIG. 6 shows a cross-sectional view of an alternative embodiment of the oblong member 65. In this embodiment, the width of at least a part of the grooves 66, when seen in a cross-sectional view, narrows down from a larger width 67 towards a smaller width 68 in the vicinity of the periphery 69 of the oblong member. As an alternative, the width may be constant in the radial direction.

In the above mentioned embodiments, the design has been focused on a catheter-like device for male users. However, the device can likewise be used by female users, with or without modifications. Due to the shorter length of the female urethra, a shorter guide member may be provided to female users. Such shorter guide members further enhance the abilities to arrange the device in a discreet and less notable configuration.

The invention claimed is:

1. A device for opening a human bladder comprising:
    an oblong member for opening the urethral sphincter and forming a distal end of the device, said oblong member being configured to open the urethral sphincter and drain fluid from the bladder into a urethra;
    a guide member fixedly coupled with the oblong member for manipulating the oblong member, at least a part of the guide member being made of an elastically deformable material flexible enough to be bent into a first configuration and then unfolding from said first configuration into a second configuration in which said guide member is sufficiently rigid in a longitudinal direction to be used to insert the oblong member into a urinary tract without buckling under longitudinal pressure associated with insertion;
    a guiding device with a compartment for guiding drained urine, the guiding device being adapted to convey the oblong member from the compartment into a urinary canal;
    a sealing element to seal between the compartment and the urinary canal; and
    a receptacle in fluid communication with the compartment of the guiding device.

2. The device according to claim 1, wherein a cross-sectional area of a major part of the guide member at least in said first configuration is substantially smaller than a cross-sectional area of the oblong member.

3. The device according to claim 1, wherein in said second configuration a cross sectional area of a major part of the guide member is smaller than a cross-sectional area of the oblong member.

4. The device according to claim 1, wherein the guide member in said first configuration is rolled.

5. The device according to claim 1, wherein at least a part of the guide member in said first configuration is bent by an essentially elastic formation of said guide member.

6. The device according to claim 1, packed in said first configuration, wherein the guide member is adapted to unfold upon un-packaging of the device.

7. The device according to claim 1, wherein the guide member is made of metal or from a polymer material or from a composite material.

8. The device according to claim 1, wherein the guide member includes a gripping element.

9. The device according to claim 1, wherein at least part of the device is provided with a surface which is hydrophilic.

10. The device according to claim 1, wherein the oblong member is solid.

11. The device according to claim 1, wherein the oblong member allows storage in a bent configuration.

12. The device according to claim 1, wherein the receptacle is formed of a flexible material allowing manipulation of the guide member through a wall of the receptacle.

13. The device according to claim 1, wherein the guide member is connected to one end of said oblong member and is in substantially linear alignment therewith.

14. A device for opening a human bladder comprising:
a solid oblong member for opening the urethral sphincter and forming a distal end of the device, said oblong member being configured to open the urethral sphincter and drain fluid from the bladder via a channel disposed along an exterior of the oblong member;
a guide member fixedly coupled with the oblong member for manipulating the oblong member, at least a part of the guide member being made of an elastically deformable material flexible enough to be bent into a first configuration and then unfolding from said first configuration into a second configuration in which said guide member is sufficiently rigid in a longitudinal direction to be used to insert the oblong member into a urinary tract without buckling under longitudinal pressure associated with insertion; and
a slack tube, the slack tube being less rigid than the oblong member, and the slack tube is longer than the guide member;
wherein the slack tube and the oblong member are provided in one piece so that the channel is fluidly coupled with the slack tube.

15. The device according to claim 14, wherein the slack tube includes a gripping element allowing the user to grip the slack tube for removing the oblong member from a urinary canal.

* * * * *